(12) United States Patent
Horng et al.

(10) Patent No.: US 7,805,179 B2
(45) Date of Patent: Sep. 28, 2010

(54) METHOD OF EXAMINING DYNAMIC CARDIAC ELECTROMAGNETIC ACTIVITY AND DETECTION OF CARDIAC FUNCTIONS USING RESULTS THEREOF

(76) Inventors: Herng-Er Horng, 4F., No. 31, Lane 57, Ta Tze St., Ta Tze, Taipei 104 (TW); Chau-Chung Wu, 2F., No. 9, Lane 74., Aigui E. Rd., Jhongjheng District, Taipei 100 (TW); Hong-Chang Yang, 4F, No. 31, Lane 57, Ta Tze St., Ta Tze, Taipei 104 (TW); Shieh-Yueh Yang, 12F., No. 427, Siyuan Rd., Sindian City., Taipei County 231 (TW)

( * ) Notice: Subject to any disclaimer, the term of this patent is extended or adjusted under 35 U.S.C. 154(b) by 500 days.

(21) Appl. No.: 11/811,391

(22) Filed: Jun. 8, 2007

(65) Prior Publication Data

US 2008/0306370 A1    Dec. 11, 2008

(51) Int. Cl.
*A61B 5/05* (2006.01)
(52) U.S. Cl. ...................................... 600/409
(58) Field of Classification Search .................. 600/409
See application file for complete search history.

(56) References Cited

U.S. PATENT DOCUMENTS

| | | | | |
|---|---|---|---|---|
| 5,603,321 | A * | 2/1997 | Kynor et al. | 600/409 |
| 6,115,628 | A * | 9/2000 | Stadler et al. | 600/517 |
| 2009/0030301 | A1* | 1/2009 | Horng et al. | 600/407 |

OTHER PUBLICATIONS

Fiona E. Smith et al., "Comparison of magnetocardiography and electrocardiography: a study of automatic measurement of dispersion of ventricular repolarization" The European Society of Cardiology 2006, Europace (2006) 8, pp. 887-893.
Petri Korhonen et a., "QRS Duration in High-Resolution Methods and Standard ECG in Risk Assessment After First and Recurrent Myocardial Infarctions" The Authors, Journal compilation 2006, PACE, vol. 29, Aug. 2006, pp. 830-836.
Yong-Ho Lee et al., "64-channel magnetocardiogram system based on double relaxation oscillation SQUID planar gradiometers" Institute of Physics Publishing, Supercond. Sci. Technol. 19 (2006), pp. S284-S288.
Kirsten Tolstrup et al. "Non-Invasive Resting Magnetocardiographic Imaging for the Rapid Detection of Ischemia in Subjects Presenting with Chest Pain" Cardiology 2006, 106, pp. 270-276.

* cited by examiner

*Primary Examiner*—Eric F Winakur
*Assistant Examiner*—Michael T Rozanski
(74) *Attorney, Agent, or Firm*—J.C. Patents

(57) ABSTRACT

A method of examining cardiac electromagnetic activity over a heart for diagnosing the cardiac functions of the heart is disclosed. The method may include constructing a phase diagram of electromagnetic signals over a heart by collecting sets of time-dependent magnetic signals, determining the zeroth and the first derivatives of each set of the magnetic signals at a given time, and categorizing the zeroth and the first derivatives of the magnetic signals in either of the four phases: (+, +), (−, −), (+, −), (−, +). The method may also include monitoring a wave propagation of the magnetic signals.

26 Claims, 7 Drawing Sheets
(5 of 7 Drawing Sheet(s) Filed in Color)

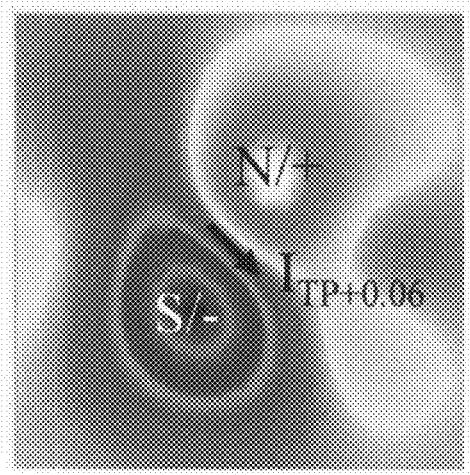
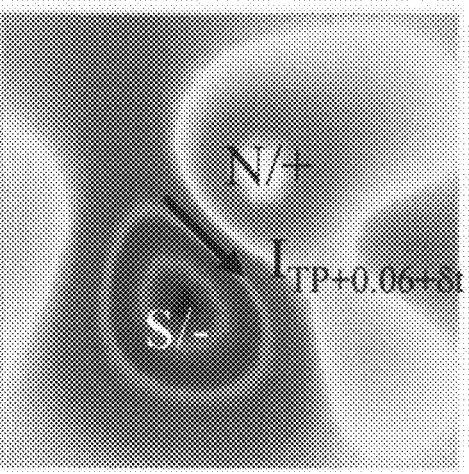
FIG. 4a      FIG. 4b
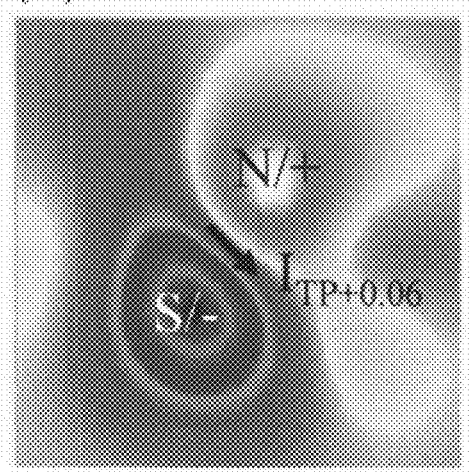
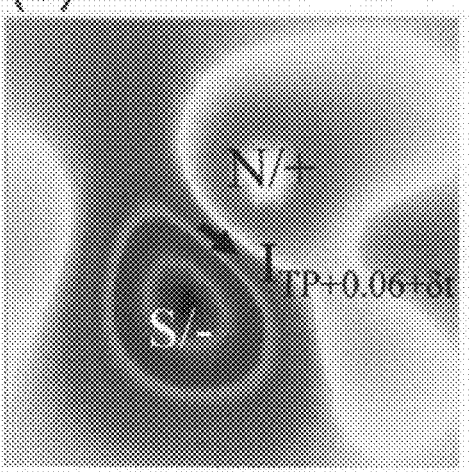
FIG. 5a      FIG. 5b

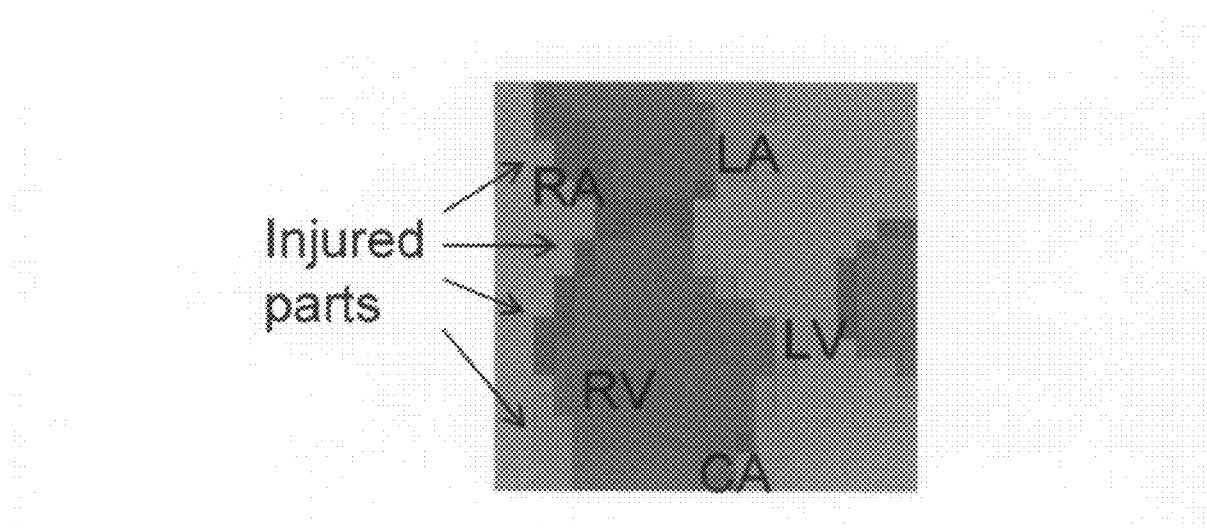
FIG. 6
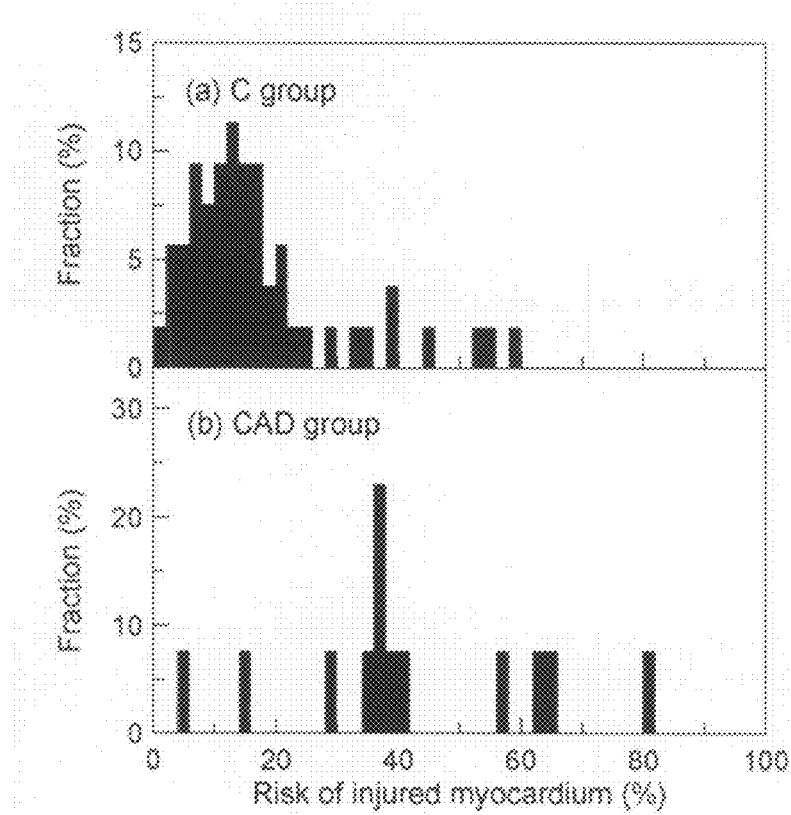
FIG. 7a
FIG. 7b

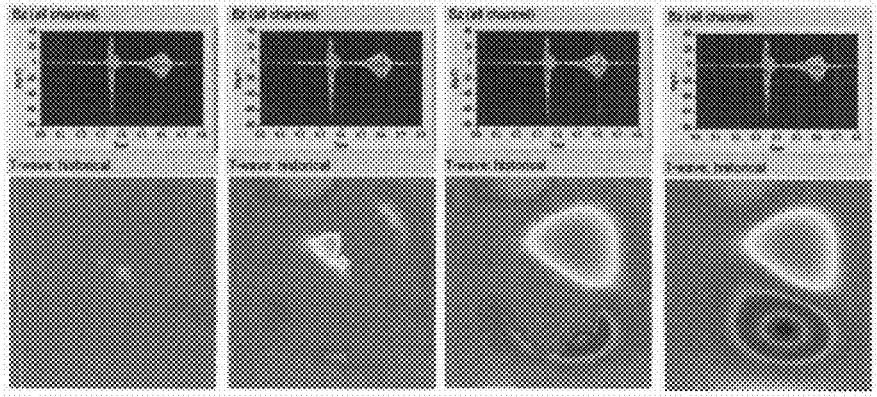
FIG. 9a  FIG. 9b  FIG. 9c  FIG. 9d
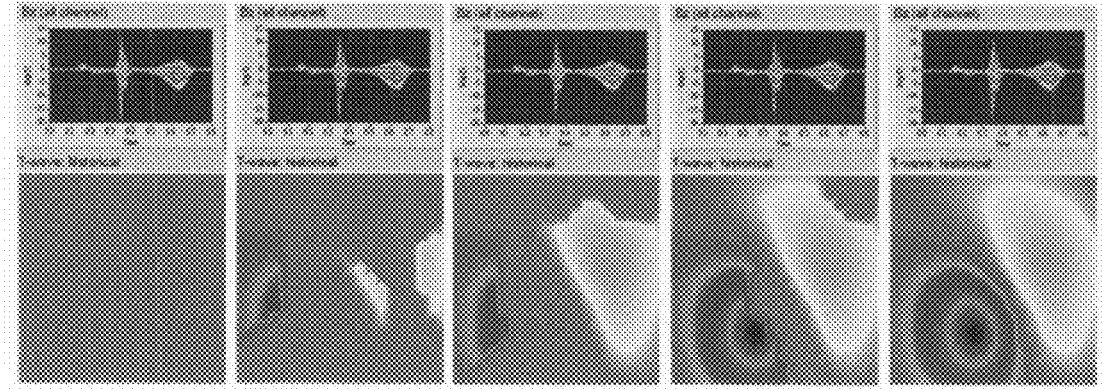
FIG.10a  FIG.10c  FIG.10e
  FIG.10b  FIG.10d

METHOD OF EXAMINING DYNAMIC CARDIAC ELECTROMAGNETIC ACTIVITY AND DETECTION OF CARDIAC FUNCTIONS USING RESULTS THEREOF

BACKGROUND OF THE INVENTION

1. Field of Invention

The present invention relates to a method of examining dynamic cardiac electromagnetic activity and a detection of cardiac functions using the results thereof. More particularly, the present invention relates to a method of examining the magnetocardiographic signals and a diagnosis of coronary artery diseases using the results thereof.

2. Description of Related Art

Each heart beat is originated from the development a small pulse of electric current that spreads rapidly in the heart and causes the myocardium to contract (depolarization and repolarization). The electrical currents that are generated spread not only within the heart, but also throughout the body, resulting in the establishment of electric potentials on the body surface, which are detectable as changes in the electrical potential with an electrocardiograph (ECG). A typical ECG tracing of a normal heartbeat (or cardiac cycle) consists of a P wave, a PR interval, a QRS complex, a ST segment, a Q-T interval, a T wave and a U wave. In brief, the P wave represents the wave of depolarization that spreads from the SA node throughout the atria; the QRS complex corresponds to the depolarization of the ventricles; the T wave represents the repolarization (or recovery) of the ventricles; the U wave, which normally follows the T wave, is not always seen and is thought to represent the repolarization of the papillary muscles or Purkinje fibers. The Q-T interval represents the time for both ventricular depolarization and repolarization to occur; the ST segment following the QRS complex is the time at which the entire ventricle is depolarized. Any normal or abnormal deflections recorded by the ECG depend upon the origin of this chain of electrical activity. Hence, via the measurements of electrical activity during a cardiac cycle, cardiac functions or pathologies can be investigated.

Although electrocardiograph (ECG) provides information related to cardiac electrical activity, the ECG signals crucially depend on the contact between the electrodes and the body. Further, in order to obtain two-dimensional signals via ECG, many electrodes need to be placed on the body, which can be impractical and may create interference between signals. Moreover, to obtain more insightful results, it is often required to perform exercise electrocardiography test, which may impose discomfort to the patient. Therefore, alternative methods that are electrode-free, contact-free and stress-free are being investigated.

Non-contact measurement technologies, such as thallium scan, computer tomography, nuclear magnetic resonance imaging, etc. have been developed, as a diagnostic tool for CAD. However, these methods require the participants to the injection of isotopes or contrast medium, or the subjection to X-ray or magnetic field, which is invasive, uncomfortable and potentially dangerous for the participants.

Many studies have demonstrated the benefit of magnetocardiography (MCG) imaging over the existing methods for certain clinical evaluation of cardiac functions and pathologies. Magnetocardiography is a noninvasive, contact-free, risk-free approach by measuring the magnetic fields of the heart generated by the same electric current as the ECG and will be altered where the electrical currents in the heart are disturbed. Although both MCG and ECG measure the cardiac depolarization and repolarization patterns, MCG may detect depolarization and repolarization in a different manner.

The magnetic signals of a beating heart can transmit through the body of a study subject and be sensed by sensors configured in proximity to but not in direct physical contact with the body. Hence, the problems in skin-electrode contact arising in ECG can be obviated. Further, MCG is less affected by the conductivity variations caused by other organs or tissues such as lung, bone and muscles. Many studies have demonstrated that MCG is potentially beneficial in various clinical applications.

However, one difficulty in obtaining the magnetocardiac signals is the weakness of the signals, which are in the order of tens of pico-Tesla for human. The superconducting quantum interference devices (SQUIDs), which exhibit a noise level less than the magnetocardiac signals by 2 to 3 orders in magnitude, have been developed to record magnetocardiac signals with an improved spatial-temporal signal resolution and a higher signal-to-noise ratio. Currently, there are many commercially available SQUID systems for detecting magnetocardiac signals. Some of these systems, which are known as multi-channel SQUID systems, may consist of many independent SQUID sensors (for example, more than 50 SQUID sensors) to allow the measurement of two-dimensional magnetocardiac signals originating from various sites over the heart. From a magnetocardiography, parameters such as $\alpha$ angles, smoothness index, current dipole moments can be estimated. Some reports have suggested that these parameters can be used as indicators for diagnosing cardiac functions or pathologies. However, other studies have indicated that these parameters overlap between normal and abnormal hearts. Hence, the existing MCG parameters are not adequate, in terms of sensitivity and specificity, for diagnosing cardiac functions or pathologies.

SUMMARY OF THE INVENTION

In view of the foregoing, the present invention provides a method of examining cardiac electromagnetic activity, wherein differentiation between a normally functioning and an abnormally functioning heart is enhanced.

The present invention also provides a method of examining cardiac electromagnetic activity, wherein localization of an injured myocardium can be achieved.

As embodied and broadly described herein, a method of examining cardiac electromagnetic activity according to a first embodiment of the invention includes constructing a phase diagram of electromagnetic signals over a heart. According to one aspect of the invention, a plurality of sets of spatially distributed, time-dependent magnetic signals is collected. Thereafter, the values of the zeroth and the first derivations of each set of the magnetic signals at a given time are determined, followed by categorizing the zeroth and the first derivations of each set of the time-dependent magnetic signals in either of four phases: (+, +), (−, −), (+, −), (−, +).

According to one aspect of the present invention, the various parts of the heart are mapped with the resulting phases to identify the functional part and the dysfunctional part of the heart.

According to one aspect of the present invention, wherein a normally functioning part of the heart has the phases of (+, +), (−, −), while an abnormally functioning part of the heart has the phases of (+, −), (−, +).

According to one aspect of the present invention, the abnormally functioning part of the heart exists at the interface of parts of the heart having phases (+, +) and (−, −).

According to one aspect of the present invention, the given time of each set of the magnetic signals is a turning point of a fitting curve to the spatially distributed, time-dependent magnetic signals at which a second derivation of the spatially distributed, time-dependent magnetic signals is zero.

According to one aspect of the present invention, each set of the spatially distributed, time-varying magnetic signals is representative of an intramyocardial, electrical behavior of the subject and comprises features of at least a P-wave, a Q-wave, a R-wave, a S-wave and a T-wave and the given time is at the turning point during a ST segment of the magnetic signals.

According to one aspect of the present invention, the first derivation of the time-dependent magnetic signals is calculated at about 0.01 to about 0.15 second after the turning point.

According to one aspect of the present invention, a risk cutoff value for screening injured myocardium can be defined with resulting phases (+, +), (−, −), (+, −), (−, +).

According to one aspect of the present invention, each set of the spatially distributed, time-varying magnetic signals is offset before the zeroth and the first derivations of the time-dependent magnetic data at a given time are determined.

According to one aspect of the present invention, the offsetting for each set of the spatially distributed, time-varying magnetic signals is accomplished by zeroing an interval of each set of the magnetic signals before a P-wave.

According to one aspect of the present invention, the magnetic signals are either two-dimensionally or three-dimensionally distributed over the heart.

According to the method of examining cardiac electromagnetic activity of the first embodiment of the present invention, by mapping the resulting phases of the magnetic signals with the various parts of the heart, the specificity of coronary artery diseases can be identified. Moreover, the injured part of the heart can be localized.

In accordance with a method of examining cardiac electromagnetic activity of a second embodiment of the present invention, the method includes monitoring a wave propagation of the magnetic signals.

According to one aspect of the invention, sets of spatially distributed, time-dependent magnetic field data of the chest, corresponding to a plurality of measurement positions, are collected. A time corresponding to a local maximum (positive or negative) intensity of the magnetic field of a wave of the magnetic field data at each measurement position is then identified, followed by plotting a temporal evolution of the local maximum intensity of the magnetic field during a time interval of the wave.

According to one aspect of the invention, the magnetic signals are either two-dimensionally or three-dimensionally distributed over the heart.

According to one aspect of the present invention, each set of the spatially distributed, time-varying magnetic field data is offset.

According to one aspect of the present invention, each set of the spatially distributed, time-varying magnetic signals is representative of an intramyocardial, electrical behavior of the subject and comprises features of at least a P-wave, a Q-wave, a R-wave, a S-wave and a T-wave.

According to one aspect of the present invention, the offsetting is accomplished by zeroing an interval of each set of the spatially distributed, time-dependent magnetic field data before a P wave.

According to one aspect of the present invention, the temporal evolution the local maximum intensity of the magnetic field during a time interval of the T wave is plotted to obtain a propagation behavior of the T wave.

According to one aspect of the present invention, the propagation behavior of a wave of a normally functioning heart and is different form that of an abnormally functioning heart.

In accordance to a method of examining cardiac electromagnetic activity of the present invention, the propagation behavior of a wave is useful in diagnosing coronary artery diseases and for localizing an injured part of the heart.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. The patent or application file contains at least one drawing executed in color. Copies of this patent or patent application publication with color drawing(s) will be provided by the Office upon request and payment of the necessary fee.

FIGS. 4(a) and 4(b) are plots of MCG contour map showing the distribution of the magnetic field $B_z$ at TP+0.06 and at TP+0.06+δt, respectively for a normally functioning heart. The effective currents at TP+0.06 at TP+0.06+δt, respectively are respectively denoted with arrows.

FIGS. 5(a) and 5(b) are plots of MCG contour map showing the distribution of the magnetic field $B_z$ at TP+0.06 and at TP+0.06+δt, respectively for an abnormally functioning heart. The effective currents at TP+0.06 at TP+0.06+δt, respectively are respectively denoted with arrows.

FIG. 6 is an exemplary 2-dimensional phase diagram of $(B_z, dB_z/dt)$ at TP+0.06 an injured heart having stenosis (>50%) at the right coronary artery (RCA).

FIG. 7(a) shows the statistical results for the risk of injured myocardium based on the distribution probabilities of the phases (+, −), (−, +) of the control group.

FIG. 7(b) shows the statistical results for the risk of injured myocardium based on the distribution probabilities of the phases (+, −), (−, +) of the CAD group.

FIGS. 9a to 9d are diagrams showing a T-wave propagation of a normal heart.

FIGS. 10a to 10e are diagrams showing a T-wave propagation of a CAD patient.

DESCRIPTION OF THE PREFERRED EMBODIMENTS

Measurements of MCG

Figure 1A:
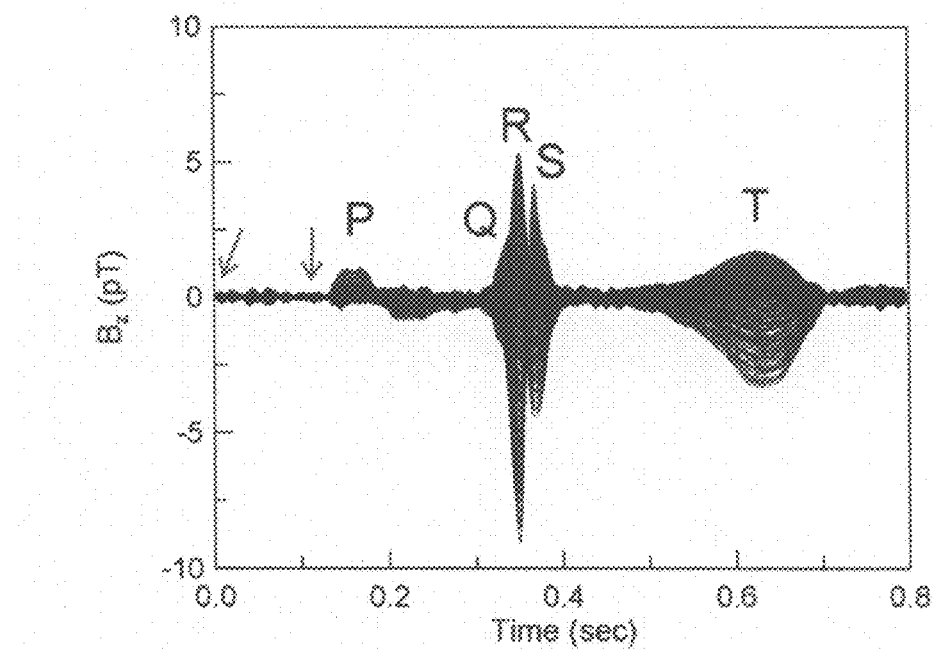
FIG. 1(a) is a diagram of $B_z$-t curves, which are plots of a collection of the spatially distributed magnetocardiac signals along the direction normal to the body surface as a function of time of a study subject using a SQUID MCG system.
Figure 1B:
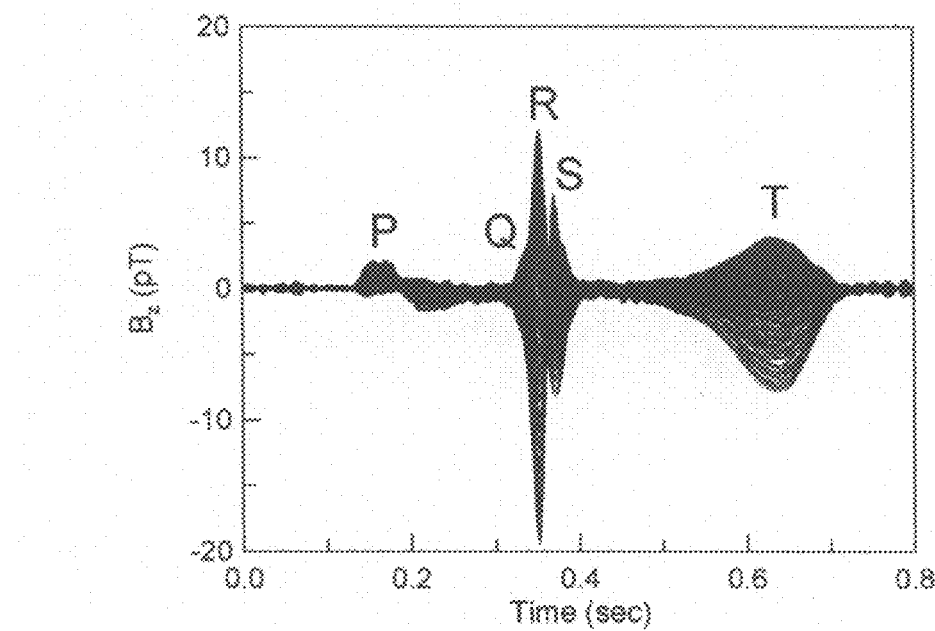
FIG. 1(b) is a diagram the spatially distributed $B_z$-t curves after zeroing by using the $B_z$'s at the pre-P wave segment.

A multi-channel SQUID system, for example, a 64-channel SQUID system or other type of sensitive superconducting magnetometers, is positioned in a plurality of coordinates, for example in a two-dimension or three-dimensional array slightly above the thorax of a live specimen. Each sensor of the SQUID system registers the local extracorporeal magnet field strength as a function of time. A MCG system normally provides measurement of the magnetic field components perpendicular (z-component) ($B_z$) to the body surface as a function of time (t). Magnetocardiograph (MCG) has features similar to the P-wave, the QRS complex, the T-wave and the U-wave of the ECG (electrocardiography). FIG. 1(a) is a diagram of $B_z$-t curves, which are plots of a collection of the spatially distributed magnetocardiac signals along the direction normal to the body surface as a function of time of a study subject using a SQUID MCG system. The collection of the magnetocardiac signals corresponds to the plurality of the measurement positions. As shown in FIG. 1(a) the P, Q, R, S, and T waves are clearly identified. However, it is worthy to note that at the pre-P wave segment of the $B_z$-t curves as indicated with two arrows in FIG. 1(a), there is a broad variation in the $B_z$ values at different positions. In principle, the value of $B_z$ at the pre-P wave segment should be zero. The variation in $B_z$'s at the different positions at the pre-P wave segment is due to the background noise. Hence, in an embodiment of this invention, the offset of each $B_z$-t curve in FIG. 1(a) is compensated by shifting the $B_z$ at the pre-P wave segment to zero. The spatially distributed $B_z$-t curves after zeroing by using the $B_z$'s at the pre-P wave segment are shown in FIG. 1(b).

With the spatially distributed $B_z$-t curves, several diagnostic parameters such as α angles in MCG contour maps, smoothness index for the QT interval, etc. can be extracted. However, it has been identified that some patients having ischemia with values of these parameters not significantly different from those of normal individuals. Hence, relying on these conventional parameters may lead to erroneous diagnosis. Accordingly, the present invention provides a method of examining the electromagnetic activity, such as magnetocardiographic signals, wherein the differentiation between a normally functioning heart and an abnormally functioning heart is enhanced. Further, in accordance to the methods of examining the electromagnetic activity of the present invention, localization of the abnormality can be achieved.

Phase Diagram Method

According to one aspect of the method of examining electromagnetic activity of the invention, the method includes constructing a phase diagram of magnetic signals, such as the magnetocardiographic signals.

Construction of Phase Diagram of Turning Points at ST Segment

Although the disclosure herein refers to certain illustrated embodiments on the construction of phase diagram of turning points at the ST segment, it is to be understood that these embodiments are presented by way of example and not by way of limitation. It should be appreciated by a person of ordinary skill practicing this invention that other intervals or waves can be used in the construction of phase diagram of turning points.

Figures 2A, 2B:
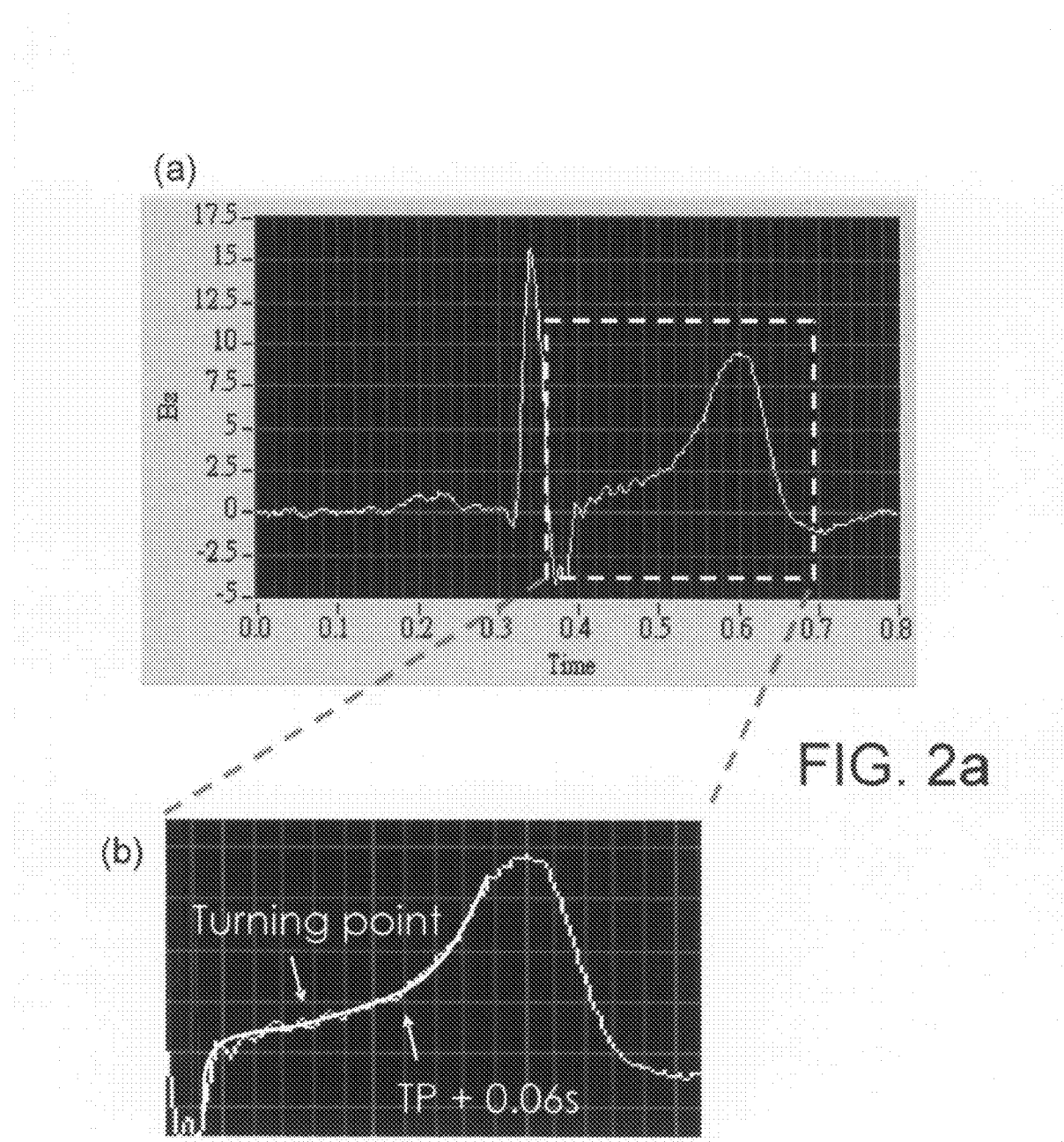
FIG. 2(a) is a plot of one of the $B_z$-t curves shown in FIG. 1(b).
FIG. 2(b) is an enlarge view of the ST-segment of the $B_z$-t curve shown in FIG. 2(a).

Referring to FIG. 2(a), FIG. 2(a) is a plot of one of the $B_z$-t curves shown in FIG. 1(b). FIG. 2(b) is an enlarge view of the ST-segment of the $B_z$ curve in FIG. 2(a). A fitting curve of polynomial function to the data in the ST segment is constructed, as presented with the yellow line in FIG. 2(b). A time point on the fitting curve is defined as a turning point. The turning point is set at which the second derivation of the fitting curve is zero, for example $d^2B_z/dt^2=0$. The corresponding time to the turning point is referred as "TP". The values of $B_z$ and $dB_z/dt$ around "TP", for example, about 0.01 to about 0.15 second after "TP", are analyzed for each measurement position. In this embodiment, the values of $B_z$ and $dB_z/dt$ around TP, for example, 0.06 second after TP (denoted as TP+0.06), are analyzed for each measurement position.

As shown in FIG. 2(a), both $B_z$ and $dB_z/dt$ at TP+0.06 are positive. Through analyzing the $B_z$-t curves for all measurement positions shown in FIG. 1(b), the zeroth and first derivation of time-dependent magnetocardiac signals ($B_z$ and $dB_z/dt$) can be categorized in either of the four phases: (+, +), (−, −), (+, −) and (−, +), and a two-dimensional phase diagram of ($B_z$, $dB_z/dt$) at TP+0.06 can be constructed.

Figure 3:
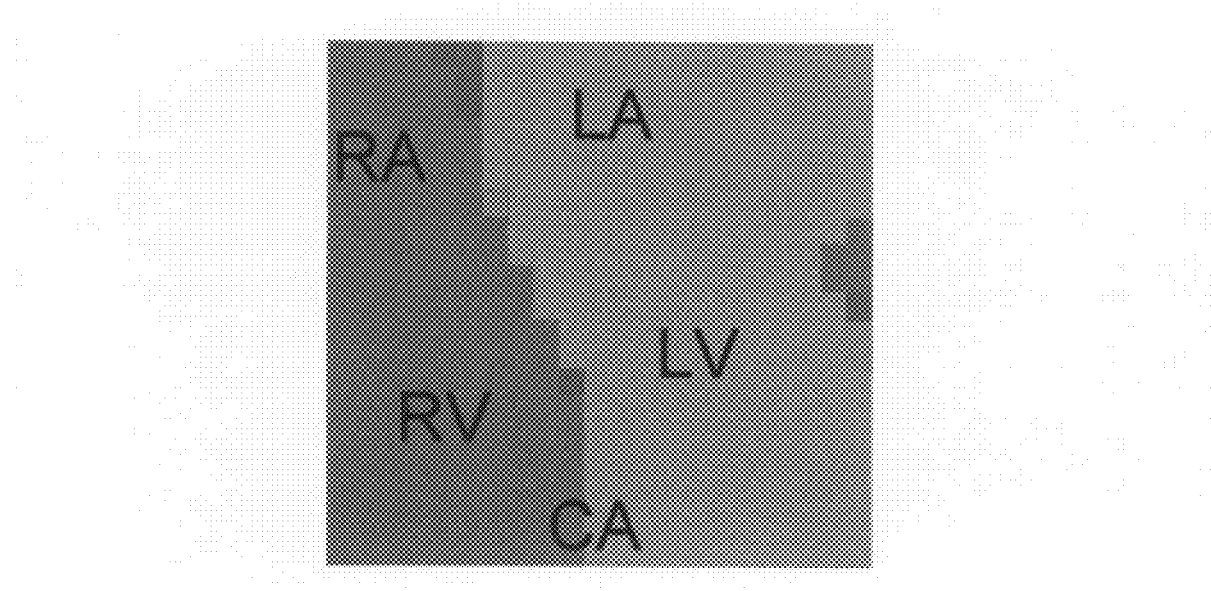
FIG. 3 is an exemplary 2-dimensional phase diagram of $(B_z, dB_z/dt)$ at TP+0.06 for a normally functioning heart.

Referring to FIG. 3, FIG. 3 is an exemplary 2-dimensional phase diagram of ($B_z$, $dB_z/dt$) at TP+0.06 for a normally functioning heart. The phase (+,+) is presented in light blue, the phase (−, −) is presented in green, the phase (+, −) is presented in red, and the phase (−, +) is presented in purple. The various parts of the heart including left atrium (LA), left ventricle (LV), right atrium (RA), right ventricle (RV) and cardiac apex (C) are mapped onto the phase diagram as labeled in FIG. 3.

Categories of $(B_z, dB_z/dt)_{TP+0.06}$ Phase from the Physiology Point of View Normal Phases of $(B_z, dB_z/dt)_{TP+0.06}$ At the time of TP+0.06, which corresponds to the beginning of the T wave, the electrical conduction along the ventricles for a normally functioning heart should become enhanced. This is normally expressed with an enhanced signal intensity of a T wave. Due to the enhancement of the electrical conduction, the magnetic signals generated by the electrical conduction are also enhanced. FIG. 4(a) is a plot of a MCG contour map via SQUID MCG measurement. A MCG contour map shows the distribution of the magnetic field obtained at specific measurement positions and the precise moments of the cardiac cycle, for example, the spatially distributed $B_z$ signals at TP+0.06. From a magnetic field map, the magnetic field extrema can be identified, and from the location of the magnetic field minima and maxima, the excitation wavefront of the effective current is determined. As shown in FIG. 4(a), a positive pole (N/+) is located at the upper-left region, and a negative pole (S/−) is located at the lower-right region. In between there exists an effective current $I_{TP+0.06}$ for the electrical conduction at TP+0.06. The effective currents at TP+0.06 and TP+0.06+δt are respectively denoted with arrows. With an infinitesimal increase in time by δt, the intensity of the effective current at TP+0.06+δt should increase, for example, $I_{TP+0.06+δt}$ as plotted in FIG. 4(b). As a result, at TP+0.06+δt, the positive magnetic signals become more positive, and the negative magnetic signals become more negative as compared with those at TP+0.06. These results imply that at the measurement positions having a positive/negative $B_z$ should show a positive/negative $dB_z/dt$. Therefore, for a normally functioning heart, $(B_z, dB_z/dt)_{TP+0.06}$ over the two-dimensional phase diagram should be mostly (+, +) or (−, −), which is evidenced with the phase diagram shown in FIG. 3.

Injured Phases of $(B_z, dB_z/dt)_{TP+0.06}$

With an injured myocardium along the conduction path, the electrical conduction could be depressed as time evolves from TP+0.06 to TP+0.06+δt. This implies that the effective current $I_{TP+0.06}+δt$ is weaker than $I_{TP+0.06}$, as illustrated in FIGS. 5(a) and 5(b). As a result, at TP+0.06+δt, the positive magnetic signals becomes less positive, and the negative magnetic signals becomes less negative as compared with those at TP+0.06. Accordingly, the measured position having a positive/negative $B_z$ shows a negative/positive $dB_z/dt$. Therefore, for an injured heart, $(B_z, dB_z/dt)_{TP+0.06}$ of (+, −) or (−, +) becomes more prominently present in the two-dimensional phase diagram.

Notably, the regions in the phase diagram of $(B_z, dB_z/dt)_{TP+0.06}$ showing (+, −) or (−, +) may correspond to the injured parts of the myocardium. For example, a phase diagram of $(B_z, dB_z/dt)_{TP+0.06}$ of an injured heart having stenosis (>50%) at the right coronary artery (RCA) is shown in FIG. 6. The function of RCA is to supply blood to the right side of the heart including the right atrium (RA) and the right ventricle (RV). If the RCA is stenotic, the myocardium at RA and RV would become ischemic or even injured. As shown in FIG. 6, the (+, +) phase is presented in light blue, the (−,−) phase is presented in green, the (+, −) phase is presented in red and the (−, +) phase is presented in purple. The various parts of the heart including left atrium (LA), left ventricle (LV), right atrium (RA), right ventricle (RV) and cardiac apex (CA) are mapped onto the phase diagram as labeled in FIG. 6. In this example of an injured heart with a stenotic RCA, $(B_z, dB_z/dt)_{TP+0.06}$ of (+, −) or (−, +) are mainly present at the RV and RA regions, which correspond to the injured parts of the myocardium at RV and RA. It is also worth to note that the phases (+, −) and (−, +) normally exist at the interface between the (+, +) phase and the (−, −) phase.

Determination of a Risk Indicator for Injured Myocardium

The phase diagram results of the present invention can be applied in risk assessment for injured myocardium. With the phase diagram results, a risk cutoff value can be defined for screening injured myocardium. Phase diagrams of $(B_z, dB_z/dt)_{TP+0.06}$ of 53 control cases (C group) and 15 cases having stenotic (>50%) coronary arteries (CAD group) are collected. For each phase diagram, such as those shown in FIG. 3 or FIG. 6, the spatial distribution probabilities of the (+, +)-phase, the (−, −)-phase, the (+, −)-phase and the (−, +)-phase are analyzed respectively. Then, the ratio of the sum of the area occupied by the (+, −)-phase and the (−, +)-phase of each individual is calculated to determine a risk indicator for injured myocardium. FIGS. 7(a) and 7(b) respectively show the statistical results for risk of injured myocardium for the C group and for the CAD group. The results indicate that there is a significant difference in the distribution of injured-myocardium risks between the control and the CAD groups. Through analyzing the receiver operating characteristic (ROC) curve, which reveals the inherent tradeoff between the sensitivity and the specificity of a test, a risk cutoff value using the data shown in FIGS. 7(a) and 7(b) was found to be 27%, which corresponds to a sensitivity of about 86.7% and a specificity of about 83.0%.

According to the results shown in FIGS. 3 and 6, it is apparent that the phase diagram of CAD patients is different from that of the normal population. Hence, via the examination on the phase diagram of the electromagnetic signals, an individual having CAD can be diagnosed. In addition, this method of the present invention affords the possibility of localizing the abnormal regions of the heart by mapping the injured phases to the regions of the heart. The application of MCG phase diagram method is not only useful for diagnostic purposes, it is also suitable for monitoring or following-up the effect of coronary intervention therapy, such as coronary artery bypass surgery, coronary angioplasty or stenting, and even after cardiac transplantation.

Wave Propagation Method

The following disclosure is directed to another aspect of the present invention of examining cardiac electromagnetic activity. The method includes monitoring a wave propagation of magnetic signals, such as the magnetocardiographic signals.

Construction of Wave Propagation of MCG

The following is an exemplary illustration on how to construct a wave propagation from the spatially distributed $B_z$-t curves. In this embodiment, the T wave propagation is analyzed. However, it should be appreciated that these embodiments are presented by way of example and not by way of limitation, and the intent of the following detailed description is to cover all modifications, alternatives, and equivalents as may fall within the spirit and scope of the invention as defined by the appended claims. For example, the wave propagation of other interval or wave of the magnetocardiography signals may be examined.

Figure 8:
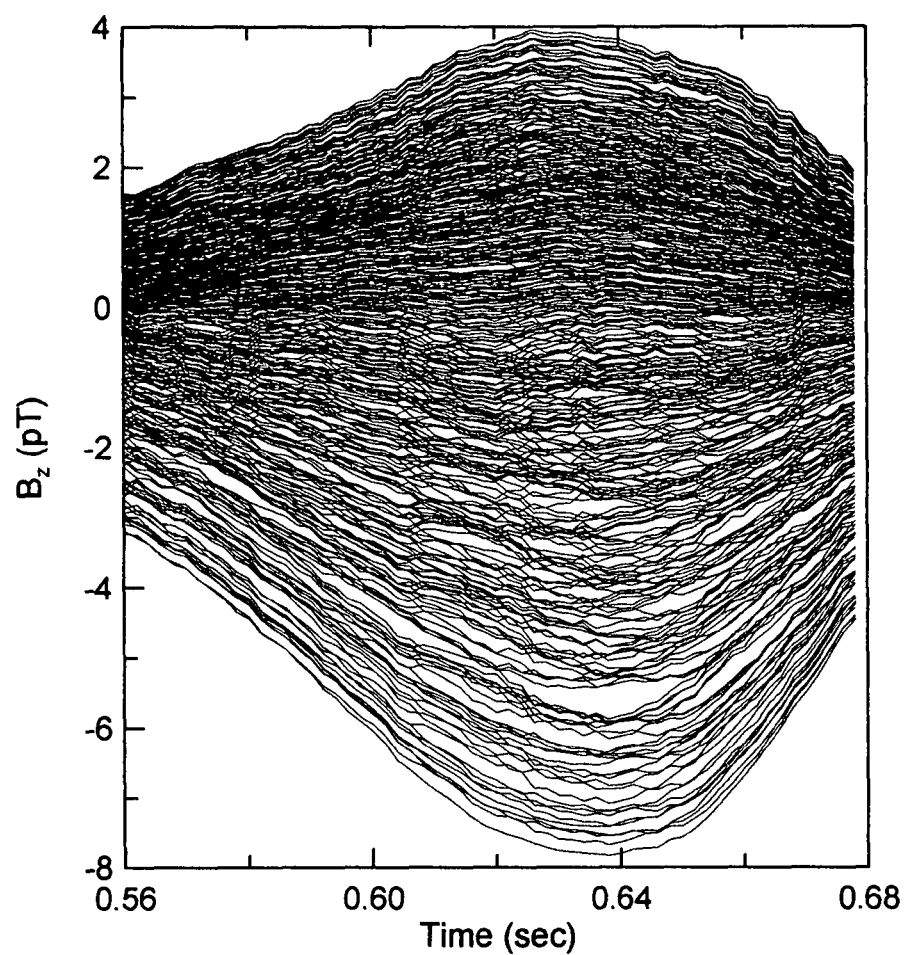
FIG. 8 is a magnified view of the T curve of a collection of $B_z$-t curves shown in FIG. 1(b).

Referring to FIG. 8, FIG. 8 is a magnified view of the collection of $B_z$-t curves shown in FIG. 1(b) at the T-wave interval. The maximum of each $B_z$-t curve at the T-wave interval occurs at different time points. Each $B_z$-t curve is usually referred as magnetocardiac signals sensed by an independent sensor channel or collected at a particular measurement position. The time corresponding to the positive/negative maximum $B_z$ of the N-th channel is defined as $t_{max,chN}$. As shown in FIG. 8, $t_{max,chN}$ of each channel varies in position in the x-y plane. As time progresses in a cardiac cycle, the positive/negative maximum $B_z$ of the N-th channel in the x-y plane at the time equal to $t_{max,chN}$ is determined. Hence, as time progresses through the T-wave interval, the two-dimensional propagation behavior of the T-wave over a heart is registered.

T-Wave Propagation of a Normal Heart Beat

The MCG's of more than 30 people with a normal heart have been collected. After analyzing the T-wave propagation of each MCG, a common behavior is identified as shown in FIGS. 9a to 9d. The top part of each of FIGS. 9(a) to 9(d) presents the collection of spatially distributed $B_z$-t curves at a particular time point, while the low part of each of FIGS. 9(a) to 9(d) presents the corresponding T-wave propagation. The red color refers to the positive (or N) pole and the blue color refers to the negative (or S) pole of MCG Notably, the left/right side of the lower part of FIGS. 9(a) to 9(d) is the right/left side of the heart under detection. According to the evolutional behaviors shown in FIGS. 9(a) to 9(d), the positive pole of T wave appears earlier than the negative pole and originates from nearly the center, slightly to the left part of the heart. This point of origination is physically close to the A-V node. Then, the positive pole propagates toward the left ventricle, and continues to the left part of cardiac apex as shown in FIGS. 9b and 9c. Finally, the T wave propagates in terms of the negative pole from the right part of the cardiac apex toward the central part through the right ventricle.

T-Wave Propagation of an Abnormal Heart Beat

The MCG's of more than 10 people with coronary artery disease (CAD) have been collected. It has been discovered that the T-wave propagations of CAD patients exhibit different behaviors from that of a normal heart as shown in FIGS. 9(a) to 9(d). Further, there are particular variations in the behaviors of the T-wave propagation among CAD patients, depending on the ischemic territory of CAD. Referring to FIGS. 10(a) to 10(e), FIGS. 10(a) to 10(e) display an example of the T-wave propagation of a CAD patient having stenotic left anterior descending (LAD) artery. Due to the stenotic LAD, some regions of the heart may become ischemic or injured. As a result, the normal path of electrical conduction through the myocardium is interrupted, which in turns modifies the path or behavior of T-wave propagation. Referring to FIG. 10(b), instead of originating from the point close to the A-V node, the T-wave in this case originates from the left ventricle in positive pole and the right ventricle in negative pole. The positive pole of T wave then propagates to the left part of cardiac apex and continues to the central part of the heart. Meanwhile, the negative pole propagates toward the right part of the cardiac apex and continues to the central part as shown in FIGS. 9(c) to 9(e).

According to the results shown in FIG. 9, it is apparent that the T-wave propagation of CAD patients is different from that of the normal population. Hence, via the examination on MCG T-wave propagation or other wave's propagation, an individual having CAD can be diagnosed. In addition, the present invention affords the possibility for localizing the abnormal regions, for example, ischemic regions, of the heart. The application of MCG wave propagation is not only useful for diagnostic purposes, it is also suitable for monitoring or following-up the effect of coronary intervention therapy, such as coronary artery bypass surgery, coronary angioplasty or stenting, and even after cardiac transplantation.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. A method of examining cardiac electromagnetic activity of a heart, the method comprising:
    performing a magnetic measurement at a plurality of measurement positions of a subject to obtain a plurality of sets of spatially distributed, time-dependent magnetic signals, corresponding to the plurality of measurement positions;
    constructing a fitting curve to each set of the spatially distributed, time-dependent magnetic signals;
    determining zeroth and first derivations of the fitting curve each set of the spatially distributed, time-dependent magnetic signals at a given time;
    categorizing the zeroth and the first derivations of the each set of the spatially distributed, time-dependent magnetic signals in one of four phases : (+, +), (−, −), (+, −), (−, +); and
    mapping the resulting phase with regions of the heart.

2. The method of claim 1, wherein the magnetic signals comprise a magnetic field component ($B_z$) normal to a surface of the subject.

3. The method of claim 1, wherein the magnetic signals are two-dimensionally or three-dimensionally distributed over a heart of the subject.

4. The method of claim 1, wherein the given time of the each set of the magnetic signals is at a turning point (TP) of the fitting curve at which a second derivation of the each set of the spatially distributed, time-dependent magnetic signals is zero.

5. The method of claim 4, wherein the plurality of sets of spatially distributed, time-dependent magnetic signals is representative of an intramyocardial, electrical behavior of said subject, and exhibits features of at least a P-wave, a Q-wave, a R-wave, a S-wave and a T-wave, and the given time is at the turning point of a ST segment of the each set of the spatially distributed, time-dependent magnetic signals.

6. The method of claim 5, wherein the each set of the magnetic signals is offset by zeroing an interval of the magnetic signals before the P-wave.

7. The method of claim 4, wherein the first derivation of the each set of the magnetic signals is calculated at about 0.01 to about 0.15 second after the turning point.

8. A method of examining cardiac electromagnetic activity for diagnosing cardiac functions of a heart, the method comprising:
    performing a non-contact magnetic measurement over a subject's thorax region at a plurality of measurement positions to obtain a plurality of sets of spatially distributed, time-varying magnetic signals of the heart of the subject, corresponding to the plurality of the measurement positions, wherein each set of the spatially distributed, time-varying magnetic signals is representative of an intramyocardial, electrical behavior of the subject and comprises features of at least a P-wave, a Q-wave, a R-wave, a S-wave and a T-wave;
    offsetting the each set of the spatially distributed, time-varying magnetic signals;
    constructing a fitting curve of polynomial function to each set of the off-set, spatially distributed, time-varying magnetic signals;
    identifying a time point on the fitting curve that corresponds to a zero value of a second derivation of the each set of the off-set, spatially distributed, time-varying magnetic signals;
    determining values of zeroth and first derivations for the fitting curve of the each set of the off-set, spatially distributed, time-varying magnetic signals at the time point corresponding to the zero value of the second derivation;
    categorizing the zeroth and the first derivations of the each set of the off-set, spatially distributed, time-varying magnetic signals in one of four phases : (+, +), (−, −), (+, −), (−, +); and
    mapping the resulting phases with regions of the heart.

9. The method of claim 8, wherein the magnetic signals comprise a magnetic field component ($B_z$) normal to a surface of the subject.

10. The method of claim 8, wherein a normally functioning region of the heart has the phases of (+, +) or (−, −), while an abnormally functioning region of the heart has the phases of (+, −), (−, +).

11. The method of claim 8, wherein the step of offsetting is accomplished by zeroing an interval of the each set of the spatially distributed, time-varying magnetic signals before a P wave.

12. The method of claim 8, wherein the first derivation of the magnetic signals is calculated at about 0.01 to about 0.15 second after the time point.

13. The method of claim 8, wherein the phases (+, −) and (−, +) exist at an interface between the phase (+, +) and the phase (−, −).

14. The method of claim 8, wherein the time point on the fitting curve that corresponds to the zero value of the second derivation of the each set of the off-set, spatially distributed, time-varying magnetic signals is at a ST segment.

15. The method of claim 8, wherein the phases (+, +), (−, −), (+, −), (−, +) are used for defining a risk cutoff value for screening injured myocardium.

16. A method of examining cardiac electromagnetic activity of a heart of a subject for diagnosing cardiac functions, the method comprising:
    performing a non-contact magnetic measurement over a thorax region of the subject at a plurality of measurement positions to obtain a plurality of sets of spatially distributed, time-varying magnetic field signals of the heart of the subject, wherein each set of the spatially distributed, time-dependent magnetic field signals at each measurement position exhibits features of at least a wave;

offsetting each set of the spatially distributed time-varying magnetic signals;

identifying a time ($t_{max,chN}$) corresponding to a local maximum (positive or negative) intensity of magnetic field of the wave of each set of the offset, spatially distributed time-varying magnetic signals at each measurement position; and plotting a temporal evolution of the local maximum intensity of the magnetic field during a time interval of the wave to obtain a propagation behavior of the wave of the each set of the offset, spatially distributed time-varying magnetic signals.

17. The method of claim 16, wherein each set of the spatially distributed, time-dependent magnetic field signals at each measurement position exhibits the features of at least a P-wave, a Q-wave, a R-wave, a S-wave, a T-wave or a combination thereof corresponding to that of an electrocardiography.

18. The method of claim 17, wherein the wave is the T-wave.

19. The method of claim 17, wherein for a normally functioning heart, a positive pole of the T-wave appears earlier than a negative pole of the T-wave.

20. The method of claim 17, wherein for a normally function heart, a positive pole of the T wave originates close to an A-V node of the heart, and propagates toward a left ventricle, and continues to a left part of a cardiac apex of the heart.

21. The method of claim 17, following an appearance of a positive pole of the T-wave at a left part of a cardiac apex of the heart, a negative of the T wave propagates from a right part of a cardiac apex toward a central part through a right ventricle.

22. The method of claim 17, wherein for an abnormally functioning heart, a positive pole and a negative pole of the T wave originate from parts of the heart different from those of a normally functioning heart.

23. The method of claim 17, wherein the each of the sets of the magnetic signals is offset by zeroing an interval of the magnetic signals before the P-wave.

24. The method of claim 16, wherein the magnetic field signals comprise magnetic field components perpendicular ($B_z$) to a surface of the subject.

25. The method of claim 16, wherein the propagation of the wave is applicable in diagnosing coronary artery diseases.

26. The method of claim 16, wherein the propagation behavior of the wave is useful in localizing ischemic regions of the heart.

* * * * *